United States Patent [19]

Rubalcaba, Jr.

[11] Patent Number: 4,898,578
[45] Date of Patent: * Feb. 6, 1990

[54] DRUG INFUSION SYSTEM WITH CALCULATOR

[75] Inventor: Bernardino Rubalcaba, Jr., Laguna Beach, Calif.

[73] Assignee: Baxter International Inc., Deerfield, Ill.

[*] Notice: The portion of the term of this patent subsequent to Jul. 12, 2005 has been disclaimed.

[21] Appl. No.: 148,554

[22] Filed: Jan. 26, 1988

[51] Int. Cl.$^4$ ............................................. A61M 5/16
[52] U.S. Cl. ........................... 604/66; 128/DIG. 13; 364/188
[58] Field of Search ............ 604/31, 50, 65–67, 604/82–83, 245; 128/DIG. 13; 364/188, 189, 172

[56] References Cited

U.S. PATENT DOCUMENTS

| | | | |
|---|---|---|---|
| 4,308,866 | 1/1982 | Jelliffe et al. | 364/413.02 |
| 4,634,426 | 1/1987 | Kamen | 128/DIG. 13 |
| 4,670,006 | 6/1987 | Sinnett et al. | 604/67 |
| 4,756,706 | 7/1988 | Kerns et al. | 604/66 |
| 4,778,449 | 10/1988 | Weber et al. | 128/DIG. 13 |

*Primary Examiner*—Dalton L. Truluck
*Assistant Examiner*—Denise W. DeFranco
*Attorney, Agent, or Firm*—Gordon L. Peterson; Debra E. Dahl

[57] ABSTRACT

A drug infusion system includes a plurality of infusion pump modules and a central management unit interconnected with the infusion pump modules to provide centralized control. The central management unit includes a touch screen for communicating with a user, the touch screen including an arrangement for enabling the user to initiate the display of a menu of infusion-rate-related parameters and selectively assign values for any of the parameters in the menu while an infusion rate value is automatically calculated according to the values so assigned. One embodiment enables temporary transfer from a titrate screen to a calculator screen with which the values are assigned, and a separate set of values is preserved for each infusion pump module.

25 Claims, 5 Drawing Sheets

DRUG INFUSION SYSTEM WITH CALCULATOR

BACKGROUND OF THE INVENTION

1. Technical Field

This invention relates generally to drug delivery systems, and more particularly to a centrally managed system with multiple infusion pumps that provide a patient with metered doses of various intravenous medications.

2. Background Information

A centrally managed, multipump, drug infusion system alleviates many concerns in such environments as intensive care units, cardiac units, operating rooms, and trauma centers. Capable of infusing several drugs simultaneously, and of doing so at different points of the body in a manner accommodating incompatible drugs, the system provides an organized complement of components suited for use under crisis conditions.

One such system includes a microprocessor-based central management unit mounted together with infusion pump modules on an IV stand. The central management unit controls the internal setup of the pump modules to cause them to function as desired. In addition, it receives and displays information from the pump modules on a touch screen that also serves as an input device with which the user can enter data and commands to the central management unit.

Aligned light-emitting diodes and phototransistors mounted on a bezel surrounding the screen provide a grid pattern of light beams which, when interrupted by the user's finger touching the screen, trigger selected control functions of the central management unit. The central management unit displays a menu of various commands or parameters, and the user simply points at the command or parameter selected. This interrupts a light beam, and the microprocessor thereafter performs accordingly.

Operation typically proceeds in one of two ways. In what may be called dosage-based operation, the physician specifies a dosage to be administered, with operation involving calculation of the corresponding infusion rate so that the infusion pump module can be controlled accordingly. In rate-based operation, however, there is no need to calculate the rate because it is specified. Instead, rate-based operation involves calculation of the corresponding dosage, this being done so that a record may be kept of the dosage that is administered.

In either case, a calculation must be made, and it is therefore desirable that the system include some means for doing this in a manner suited to crisis conditions. The calculation procedure should be quick and convenient with little chance for user confusion and error, and it should facilitate medication adjustments according to patient reaction.

Although calculators exist, they are not configured for this special function. With some calculators, for example, the specified dosage or infusion rate must be entered along with other necessary parameter values. Then, the solution (infusion rate or dosage) is displayed, and this value must be transferred to the corresponding infusion pump module, the process taking time and effort and risking error.

Furthermore, data for one infusion pump module is often lost when the calculator is used for another infusion pump module, and this compounds the problem. In addition, it is sometimes desirable to perform dose and infusion rate calculations during titration procedures, and existing calculator arrangements are inconvenient to use for this purpose. Consequently, it is desirable to have a system with a calculator function that overcomes these concerns.

SUMMARY OF THE INVENTION

This invention solves the problems outlined above by providing a system with a touch screen calculator arrangement that automatically calculates, displays, and stores a separate set of parameter values for each one of the infusion pump modules. As the user changes a displayed value utilizing touch screen techniques, the system automatically updates the displayed dosage and infusion rate values accordingly, with the updated infusion rate value being stored and immediately available for control purposes.

Thus, the data entry and calculation procedure is quick and convenient with far less chance for user confusion and error. It proceeds in a manner suited to crisis conditions and it greatly facilitates medication adjustments according to patient reaction. Moreover, it provides the basis for quick and convenient calculation during titration procedures.

Generally, a drug infusion system constructed according to the invention includes a plurality of infusion pump modules and a central management unit that is interconnected with the infusion pump modules to provide centralized control. The central management unit includes a touch screen for communicating with a user that includes an arrangement for enabling the user to initiate the display of a menu of infusion-rate-related parameters and selectively assign values for any of the parameters in the menu.

According to a major aspect of the invention, there is provided components for automatically calculating an infusion rate value according to the values so assigned for purposes of controlling the infusion pump modules accordingly. The menu of parameters may include an infusion rate parameter, a dosage parameter, a volume-of-solution parameter, a weight-of-drug parameter, and a body weight parameter, and calculations and displayed values are automatically updated when the value of any parameter is changed.

According to another aspect of the invention, the assigned and calculated values are stored so that the calculator function can be utilized for any one of the infusion pump modules without losing data already entered for the other ones of the modules.

According to yet another aspect of the invention, calculations can be performed in the midst of titration procedures. This is accomplished by providing a titration screen from which a calculator screen can be selected so that the user can transfer rapidly back and forth between the titration screen and the calculator screen for each of the infusion pump modules, with separate values being stored for each module.

The above mentioned and other objects and features of the invention and the manner of attaining them will become apparent, and the invention itself will be best understood, by reference to the following description taken in conjunction with the accompanying illustrative drawings.

DESCRIPTION OF THE PREFERRED EMBODIMENT

Figure 1:
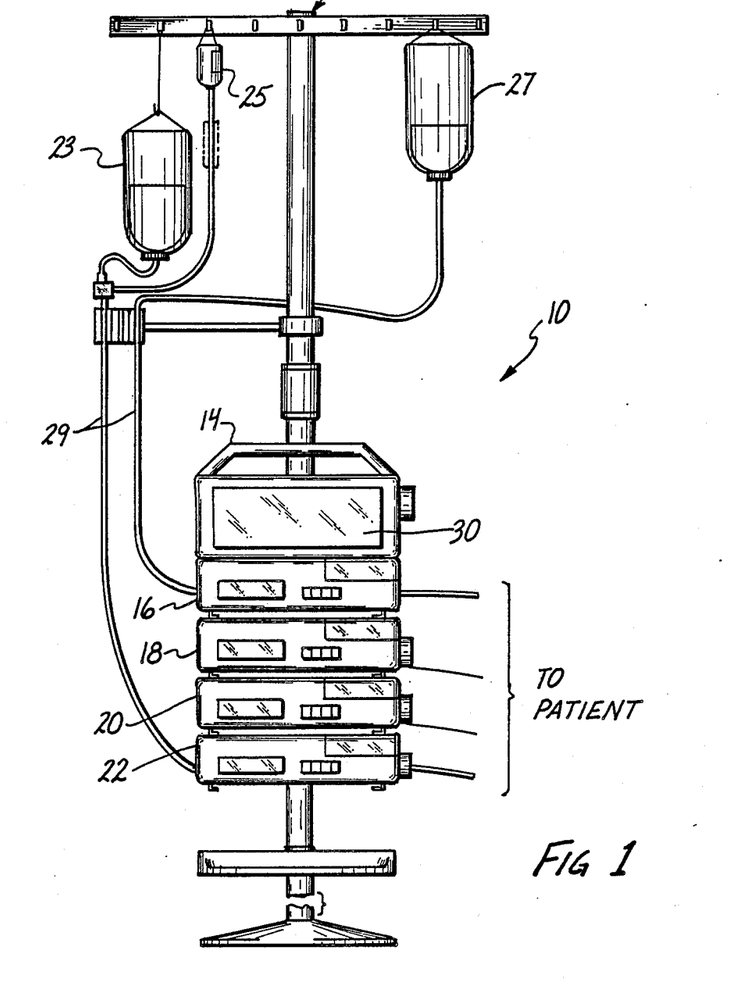
FIG. 1 of the drawings is a front elevation view of an IV stand supporting a drug infusion system constructed according to the invention.

Referring now to FIG. 1, there is shown an infusion system 10 constructed according to the invention that is mounted on an IV stand 12. The system 10 includes a central management unit 14 that is interconnected with a plurality of infusion pump modules 16, 18, 20, and 22, the modules providing a patient with metered doses of various intravenous medications under centralized control of the central management unit 14. Fluid flows from a plurality of IV bottles 23, 25, and 27 and through cannulae 29 to the infusion pump modules for this purpose, with the central management unit 14 controlling such aspects of operation as an infusion rate for each of the modules (i.e., the rate at which the medications are administered).

The system 10 is similar in many respects to the system described the U.S. patent issuing from the U.S. patent application Ser. No. 821,153 filed Jan. 21, 1986, entitled "Centrally Managed Modular Infusion Pump System." That patent and application are incorporated by reference for the details of the system described.

The central management unit 14 includes a touch screen 30 and associated components subsequently described that serve as means for enabling a user to communicate with the unit 14. The touch screen 30 and associated components are similar to the touch screen arrangement described in above-referenced patent, providing a display output while serving as a touch input device with which the user can enter data and commands to the central management unit 14 by pointing at selected areas of the touch screen 30 that are identified by the display.

Figure 2:
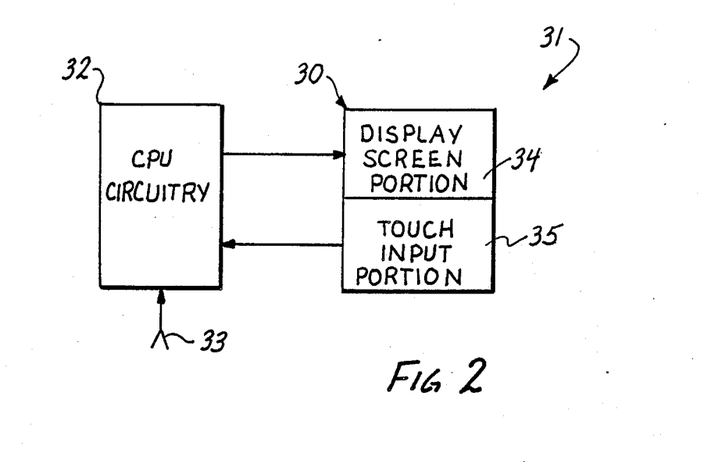
FIG. 2 is a schematic block diagram of the system.

The touch screen 30 and associated components provide the touch screen arrangement 31 illustrated in FIG. 2. This is part of the central management unit 14, and it includes central processing unit circuitry 32 and an output port 33 to which the infusion pump modules can be connected. The CPU circuitry 32 may include a conventional microprocessor chip with suitable programming, memory, and supporting circuitry that are not individually shown. These elements may be configured as described in the above-referenced patent, and the programming may be conventionally implemented to accomplish the dialogue and other functions subsequently described.

Control information is passed between the CPU circuitry 32 and the infusion pump modules through the output port 33, while a dialogue or communications between the user and the CPU is accomplished by using the CPU circuitry 32 to display information on the display screen portion 34 of the touch screen 30 and receive information from the touch input portion 35, the touch input portion 35 including a grid pattern of light beams that the user interrupts when pointing at a selected area of the display screen portion 34.

Figure 3:
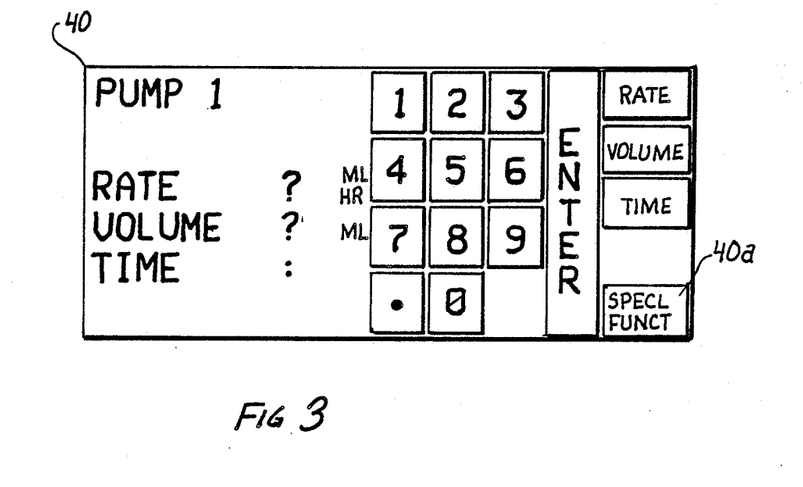
FIGS. 3-9 depict various displays utilized in the system.

The invention includes means for enabling the user to initiate the display of a menu of infusion-rate-related parameters. This is accomplished in the illustrated embodiment with the touch screen arrangement 31 and a primary entry display 40 (FIG. 3). The primary entry display 40 may be utilized to designate a selected one of the infusion pump modules as described in the abovereferenced patent PUMP 1 is designated in FIG. 3, this being the designation for the infusion pump module 16.

In addition, the primary entry display 40 includes an area designated "SPECL FUNCT" as an abbreviation for "special function." This provides a special function key 40A, and when the user selects the "SPECL FUNCT" by pointing at the key 40A, the CPU circuitry 32 causes a special functions display 41 (FIG. 4) to be displayed.

Figures 4, 5:
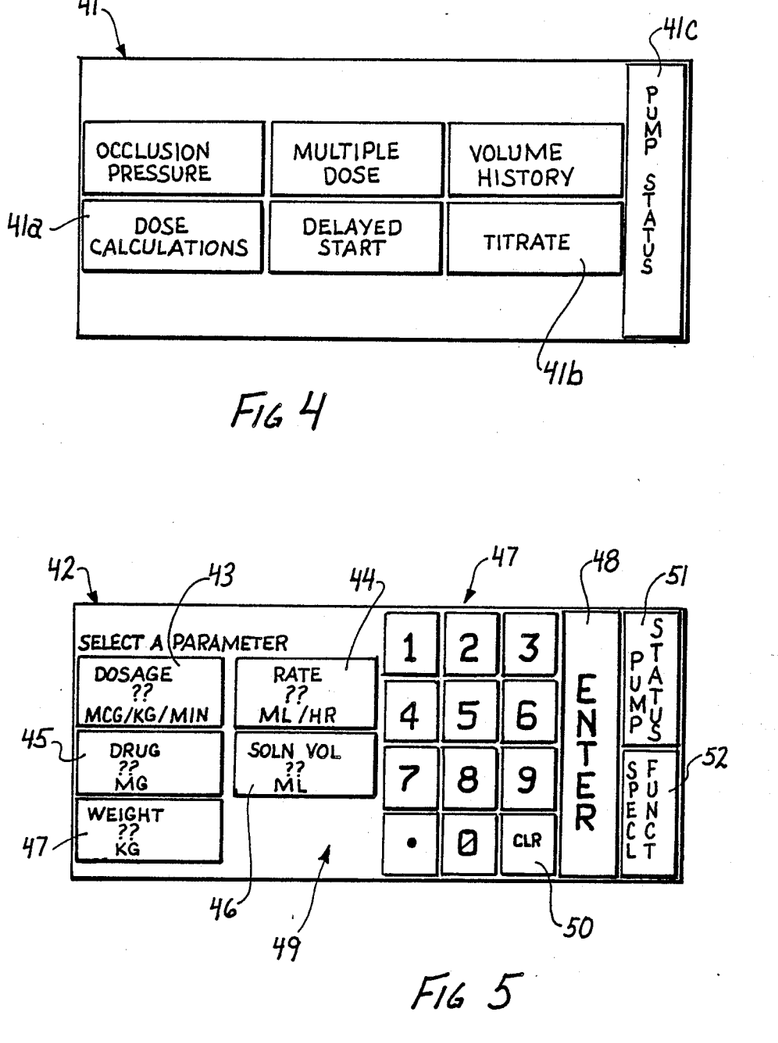

The display 41 is used to select one of the special functions identified on that display for the designated infusion pump module, in this case PUMP 1 or infusion pump module 16. It includes an area designated "DOSE CALCULATIONS" (i.e., a dose calculator key 41A) and selecting this area results in the display of a calculator display 42 (FIG. 5). It also includes a titrate key 41B for use in selecting a titrate display subsequently described with reference to FIGS. 8 and 9, and a pump status key 41C that is selected to return to the primary entry display 40.

The calculator display 42 has a menu or list of infusion-rate-related parameters. The menu includes an area designated "DOSAGE" for a dosage parameter. This may be referred to as a dosage key 43. The menu also includes areas designated "RATE" for an infusion rate parameter (an infusion rate key 44), "DRUG" for a weight-of-drug parameter (a drug key 45), and "SOLN VOL" for a volume-of-solution parameter (a solution key 46). The calculator display 42 also includes an area designated "WEIGHT," for a body weight parameter (a weight key 47), but this parameter may be absent in certain operational modes subsequently described.

The system 10 calculates either dosage, infusion rate, weight of drug, or volume of solution from the remaining ones of those parameters using one of the following formulae:

$$r = (d_W W V)/R_x \quad (1)$$

$$r = (dWV)/R_x \quad (2)$$

where:
r = infusion rate
$d_W$ = dosage per unit of body weight per unit of time;
d = dosage per unit of time;
W = body weight (an input parameter that cannot be calculated);
V = volume of solution; and
$R_x$ = weight of drug.

For formulae (1), the user needs to assign a value for the body weight parameter and for three of the other four parameters in order for the system 10 to calculate the fourth parameter. For formula (2), the user needs to assign a value for three out of the four parameters and the system 10 will calculate the corresponding value for the fourth parameter.

The units for the amount-of-drug parameter ($R_x$), the weight parameter (W), and the dosage parameter (d or $d_W$) are selectable. For the amount-of-drug parameter, the possible units are grams, milligrams, and micrograms. These are designated on the display 42 by the abbreviations GM, MG, and MCG, respectively.

For the dosage parameter, the possible units are micrograms per kilogram per minute, milligrams per minute, and micrograms per minute. These are designated by the abbreviations MCG/KG/MIN, MG/MIN, and MCG/MIN.

When the user selects a parameter that has selectable units, the alternatives appear on the bottom of the display 42 to the left of a keypad 47 and an enter key 48 in the area designated generally at 49. The user selects a parameter and the desired units, and then presses the enter key 48. This changes the units for the selected parameter whether or not a value is keyed in for that parameter.

Figure 6:
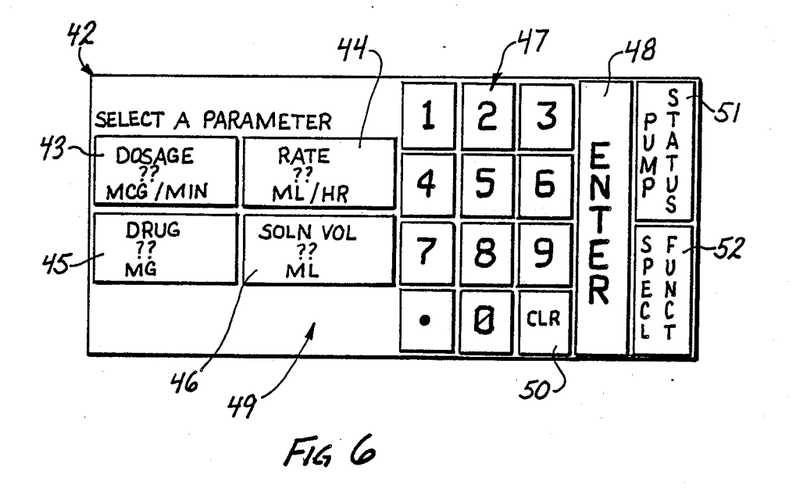

When formula (1) is being used, the body weight parameter appears in the lower left hand corner of the display 42 as the weight key 47 (FIG. 5). When formula (2) is being used, the body weight parameter is absent from the display 42 as illustrated in FIG. 6. Selection of formula (1) or formula (2) is done automatically by the system 10 according to the units selected for the dosage parameter. If the units selected for the dosage parameter are micrograms per kilogram per minute (MCG/KG/MIN), formula (1) is used. If the units selected are milligrams per minute (MG/MIN) or micrograms per minute (MCG/MIN), formula (2) is used.

Figure 7:
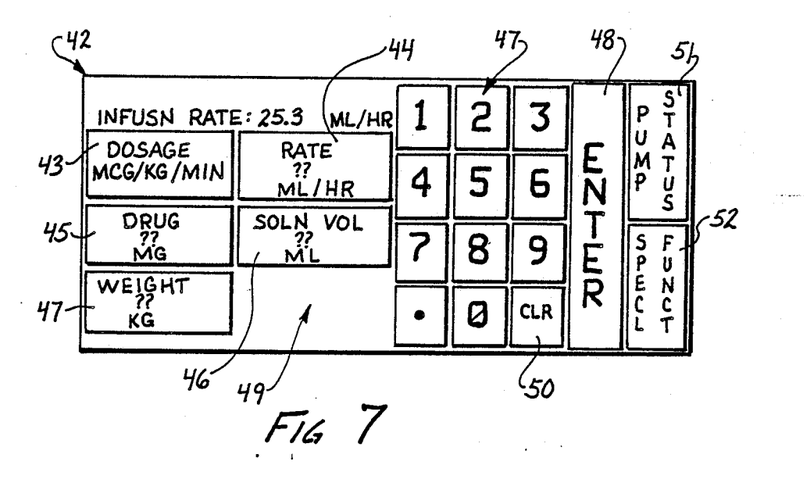

The invention includes means for enabling the user to selectively assign values for any of the parameters in the menu. This is accomplished in the illustrated embodiment with the touch screen arrangement 31 by having the display 42 include the numeric keypad 47 and the enter key 48. The user selects one of the infusion-rate-related parameters in the menu described above, selects the units if different from the units displayed, and keys in a value for that parameter on the keypad 47. As this is done, a parameter-identifying prompt (such as "INFUSN RATE" in FIG. 7) and the keyed-in value (shown by way of example as the value 25.3 in FIG. 7) appear above the menu of parameters, and these are entered when desired by the user selecting the enter key 48.

Once a value is entered, it is displayed adjacent the parameter in the menu. Calculated values are also displayed in this way. Until a value is entered or calculated, a pair of question marks (??) appear in the display 42 in its place as shown in FIGS. 5-7 and 9. But, once a value is entered or calculated, it replaces the appropriate pair of question marks.

The area designated "CLR" (i.e., a clear key 50) is used to clear an individual entry from the prompt line before the enter key 48 is selected. It may also be used to clear all of the values assigned for the parameters by first selecting the clear key 50 and then selecting the enter key 48.

An area designated "PUMP STATUS" in FIGS. 4-7 (a pump status key 51) is used to return to the primary display 40 shown in FIG. 3, and an area designated "SPECL FUNCT" (a special function key 52) is used to return to the special function display 41 shown in FIG. 4.

The invention includes means for automatically calculating an infusion rate value according to the values assigned for the parameters, and this is done with the CPU circuitry 32 according to the appropriate one of the formulae (1) and (2) described above. Calculation are automatically redone when the value of a parameter is changed, and the new values are automatically displayed. The user selects a parameter and enters a new value. If the value of the infusion rate parameter is changed, a new value for the dosage parameter is calculated. However, if it is not the value of the infusion rate parameter that is changed, then a new value for the infusion rate parameter is calculated.

All of the parameters have minimum and maximum permissible values in the system 10. These are as follows:

| Parameter | Units | Minimum | Maximum |
|---|---|---|---|
| Body Weight | KG | .1 | 454.5 |
| | LBS | .1 | 999.9 |
| | GM | .1 | 999.9 |
| Dosage | MCG/KG/MIN | .01 | 999.99 |
| | MCG/MIN | .01 | 999.99 |
| | MG/MIN | .1 | 999.9 |
| Infusion Rate | ML/HR | .1 | 99.9 |
| | ML/HR | 1 | 999 |
| Drug Weight | MG | .1 | 9999 |
| | MCG | .1 | 9999 |
| | GM | .1 | 9999 |
| Solution Volume | ML | .1 | 99.9 |
| | ML | 1 | 3000 |

If the user enters a value that is not within the above limits, the value will be displayed along with an indication that it is invalid and an indication of the valid range. Also, if a calculated value is out of range, this is also indicated. These indications are made in an area of the display 42 above the menu of parameters.

According to another aspect of the invention, there is provided means for storing the values that are assigned and calculated for the parameters. In the illustrated embodiment, the CPU circuitry 32 functions to serve this purpose. It includes suitable programming and sufficient memory to accomplish this storage function so that the various values of the parameters need not be reentered.

According to yet another aspect of the invention, calculations can be performed conveniently in the midst of titration procedures. This is accomplished by providing a titration display or screen 60 (FIG. 8) from which a calculator display or screen 61 (FIG. 9) can be selected so that the user can transfer rapidly back and forth between the titration screen 60 and the calculator screen 61 for each of the infusion pump modules, with separate values being stored for each module.

Figure 8:
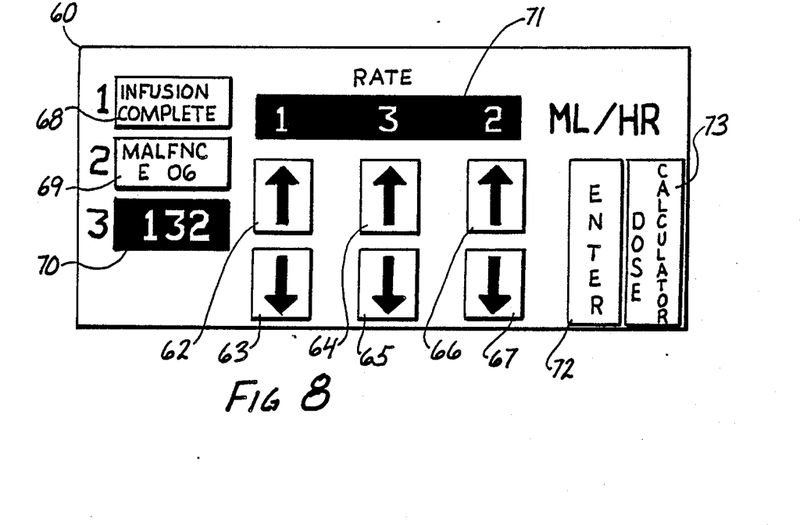

The titration screen 60 is, in a broad sense, a screen arranged to be used in a titration mode of operation. It includes up and down buttons or keys that allow the user to modify the infusion rate for each of the infusion pump modules quickly, and it is selected by pointing at the titrate key 41B on the special functions display 41 (FIG. 4).

The selected infusion pump module, PUMP 1 corresponding to the infusion pump module 16, is the selected infusion pump module for titration. The titration display 60 has up and down arrow keys 62–67. The first pair, the arrow keys 62 and 63, can increment or decrement the hundreds place, the second pair, the arrow keys 64 and 65, can increment or decrement the tens place, and the third pair, the arrow keys 66 and 67, can increment or decrement the units place. There is no decimal point or decimal place for the infusion rate in the titration mode.

To the left of the up and down arrow keys 62–67 are the select keys 68–70 for each infusion pump module, with the current rate for the infusion pump module shown within the key. On the left of each one of the select keys 68–70 is a designation of the infusion pump modules position in the system 10. An infusion pump module is selected for titration by touching the select key for that infusion pump module, whereupon the infusion rate appears above the up and down arrow keys in reverse video in the area of the titration screen 60 below the word "RATE" (i.e., a window 71 in FIG. 8). Also, the select key appears in reverse video as depicted by the select key 70 in FIG. 8.

To change the infusion rate on the selected infusion pump module, the user changes the rate in the window 71 to the required amount by using the appropriate ones of the arrow keys 62-67. The up arrow keys (the keys 62, 64, and 66) increase the digit and the down arrow keys (the keys 63, 65, and 67) decrease the digit by one for each key touch. Also, the up arrows allow for carry over while the down arrows allow for borrow. The rates that are available are from one to 999 ML/HR.

After the infusion rate is changed, an enter key 72 begins flashing. When the enter keys 72 is pressed, the selected infusion pump module begins infusing at the new rate and the new rate is shown in the appropriate select key.

The titration screen 60 includes an area designated "DOSE CALCULATOR" (i.e., a dose calculator key 73). This is used to perform dose calculations and then return to the titrate screen. Selecting the dose calculator key 73 causes the display of the titration calculator screen 61 shown in FIG. 9. This is used to calculate the infusion rate to be entered for titration purposes, as described above with reference to the calculator display 42.

Figure 9:
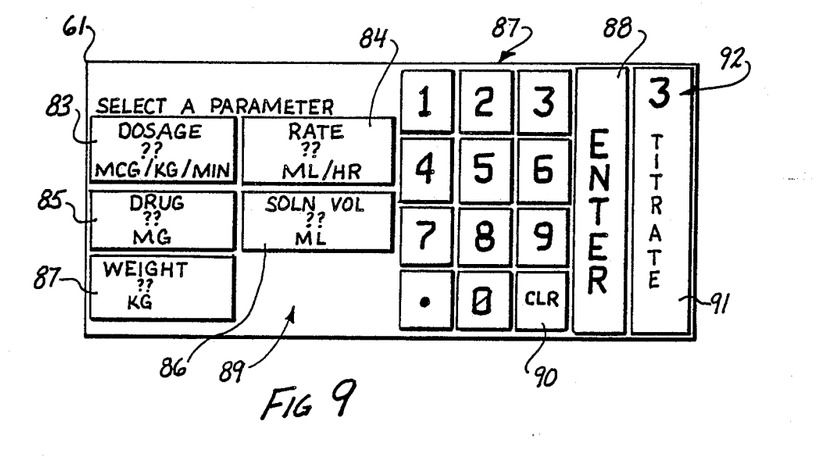

The titration calculator screen 61 is, in a broad sense, a screen arranged to be used in a calculator mode of operation. It includes a menu of parameters that the user can assign values to for purposes of having the central management unit calculate other parameter values, and it is generally similar in layout and operation to the calculator display 42. In this regard, reference numerals designating many aspects of the titration calculator screen 61 are increased by forty over those designating similar aspects of the calculator display 42. These include a plurality of keys 83-88 and 90 that correspond to the keys 43-48 and 50 for the calculator display 42, and an area 89 that corresponds to the area 49. These similar features are not further described.

One important difference is that the titration calculator screen 61 includes an area designated "TITRATE" (i.e., a titrate screen key 91). When the dose calculator key 73 is selected on the titrate screen 60, the user can perform dose calculations only for the selected one of the infusion pump modules and return only to the titrate screen 60. Return to the titrate screen 60 is accomplished by selecting the titrate screen key 91.

The currently selected infusion pump modules is identified on the titration key 91, in an area designated by numeral 92 (FIG. 9). When the rate is calculated using the titration calculator screen 61 and the user returns to the titration screen 60, the calculate rate appears above the arrow keys in the area 71 (FIG. 8) and the enter key 88 flashes until the user selects the enter key to confirm the new rate.

Once a calculation is made for an infusion pump module on the titration calculator screen 61, the entered parameter values are saved for that infusion pump module. The calculations for each of the infusion pump modules are saved separately, and if the user returns to the titration calculator screen 61, the previously entered values for the selected infusion pump module are displayed on the titration calculator screen 61.

If the user has entered a new rate for an infusion pump module using the arrow keys on the titration screen 60 (FIG. 8), the new rate and the new calculated dosage is reflected on the titration calculator screen 61.

The above is accomplished with the touch screen arrangement 31 illustrated in FIG. 2, utilizing suitable programming to accomplish the displays, calculations, storage, and other functions described.

In other words, the central management unit includes transfer means for enabling the user to transfer between the titrate screen and the calculator screen. This is accomplished with suitable programming. Similarly, the transfer means may include means for enabling the user to return from the calculator screen only to the titrate screen, the calculator means may include means for automatically updating the values of the parameters according to a new infusion rate entered by the user with the titrate screen, and the central management unit may include means for storing the values that are assigned and calculated for the parameters. These functions are all accomplished with suitable programming also.

In operation, the user first defines the volume for each infusion pump module with the primary entry display 40 (FIG. 3). Next, the user presses the special function key 40A on the primary entry display 40 to get into the special function display 41 (FIG. 4), and then the titrate key 41B on the special function display 41 to get into the titrate screen 60 (FIG. 8) from which an individual titrate calculator is available for each of the infusion pump modules.

The user selects the titrate calculator with the dose calculator key 73 on the titrate screen 60 (FIG. 8), and then enters values for the parameters to get the infusion rate. This is entered with the titration screen 60, and titration proceeds accordingly.

Thus, this invention provides a system with a touch screen calculator arrangement that automatically calculates, displays, and stores a separate set of parameter values for each one of the infusion pump modules. The data entry and calculation procedure is quick and convenient. There is far less chance for user confusion and error. Use proceeds in a manner suited to crisis conditions and in a manner that facilitates medication adjustments according to patient reaction, and the user can rapidly and conveniently perform calculations with the touch screen arrangement during titration procedures.

Although an exemplary embodiment of the invention has been shown and described, many changes, modifications, and substitutions may be made by one having ordinary skill in the art without necessarily departing from the spirit and scope of this invention.

What is claimed is:

1. A drug infusion system, comprising:
   a plurality of infusion pump modules and a central management unit interconnected with the infusion pump modules to provide centralized control, the central management unit including means for communicating with a user that includes:
   (a) means for enabling the user to initiate the display of a menu of infusion-rate-related parameters;
   (b) means for enabling the user to selectively assign values for any of the parameters in the menu; and
   (c) means for automatically calculating an infusion rate value according to the values so assigned for purposes of controlling the infusion pump modules accordingly.

2. A system as recited in claim 1, wherein the menu of infusion-rate-related parameters includes:

an infusion rate parameter;
a dosage parameter;
a volume-of-solution parameter; and
a weight-of-drug parameter.

3. A system as recited in claim 2, wherein the means for automatically calculating includes:
means for calculating an infusion rate value based on the formula:

$$r = (dWV)/R_x$$

4. A system as recited in claim 1, wherein the menu of infusion-rate-related parameters includes:
an infusion rate parameter;
a dosage parameter;
a volume-of-solution parameter;
a weight-of-drug parameter; and
a body weight parameter.

5. A system as recited in claim 4, wherein the means for automatically calculating includes:
means for calculating an infusion rate value based on the formula:

$$r = (dWWV)/R_x$$

6. A system as recited in claim 1, wherein the means for automatically calculating includes:
means for automatically calculating a value for the dosage parameter that corresponds to the value for the infusion rate.

7. A system as recited in claim 6, wherein:
the value calculated for the dosage parameter represents dosage-per-unit-of-time.

8. A system as recited in claim 6, wherein:
the value calculated for the dosage parameter represents dosage-per-unit-of-body-weight-per-unit-of-time.

9. A system as recited in claim 1, wherein the means for enabling the user to selectively assign values for any of the parameters in the menu includes:
the display having a numeric keypad likeness with which the user can enter values.

10. A drug infusion system as recited in claim 1, wherein the central management unit includes:
means for storing the values that are assigned and calculated for the parameters.

11. A system as recited in claim 1, wherein the means for communicating with a user includes:
a touch screen arrangement.

12. A system as recited in claim 11, wherein the means for enabling the user to initiate the display of a menu of infusion-rate-related parameters includes:
a touch screen display having an image that the user selects to initiate the display of the menu.

13. A system as recited in claim 1, wherein the means for communicating with the user includes:
means for displaying values for the parameters;
means for enabling the user to selectively change any one of the values so displayed; and
means for automatically updating the other ones of the values when such a change is made.

14. A system as recited in claim 1, wherein the means for communicating with a user includes:
a titrate screen arranged the infusion pump modules for titration purposes; and
calculator means for enabling the user to initiate infusion-rate-related calculations from the titrate screen.

15. A system as recited in claim 14, wherein:
the calculator means includes a calculator screen; and
the central management unit includes transfer means for enabling the user to transfer between the titrate screen and the calculator screen.

16. A system as recited in claim 15, wherein:
the transfer means includes means for enabling the user to return from the calculator screen only to the titrate screen.

17. A system as recited in claim 14 wherein the calculator means includes:
means for automatically updating the values of the parameters according to a ne infusion rate entered by the user with the titrate screen.

18. A system as recited in claim 14, wherein the central management unit includes:
means for storing the values that are assigned and calculated for the parameters.

19. A drug infusion system, comprising:
a plurality of infusion pump modules and a central management unit interconnected with the infusion pump modules to provide centralized control, the central management unit including means for communicating with a user that includes:
(a) a titrate screen to be used for titration purposes;
(b) means for enabling the user to initiate the display of a menu of infusion-rate-related parameters from the titrate screen;
(c) means for enabling the user to selectively assign values for any of the parameters in the menu; and
(d) means for automatically calculating an infusion rate value according to the values so assigned for purposes of controlling the infusion pump modules accordingly from the titrate screen.

20. A system as recited in claim 19, wherein the central management unit includes:
means for storing values for the parameters for each of the infusion pump modules.

21. A system as recited in claim 19, wherein the central management unit includes:
means for updating the stored values according to a new infusion rate entered with the titrate screen.

22. A drug infusion system, comprising:
a plurality of infusion pump modules and a central management unit interconnected with the infusion pump modules to provide centralized control, the central management unit including touch screen means for communicating with a user that includes:
(a) a titrate screen to be used for titration purposes;
(b) a calculator screen to be used for calculation purposes, including a menu of infusion-rate-related parameters;
(c) means for enabling the user to initiate the display of the calculator screen from the titrate screen;
(d) means for enabling the user to selectively assign values for any of the parameters in the menu utilizing touch screen techniques; and
(e) means for automatically calculating an infusion rate value according to the values so assigned for purposes of controlling the infusion pump modules accordingly.

23. A system as recited in claim 22, wherein in the central management unit includes:
means for enabling the user to selectively change the value of the infusion rate parameter from the titrate screen; and means for automatically updating the values when such a change is made.

24. A drug infusion system, comprising:

a plurality of infusion pump modules and a central management unit interconnected with the infusion pump modules to provide centralized control;

the central management unit including touch screen means for communicating with a user;

the touch screen means including a titration screen to be used in a titration mode of operation and a calculator screen to be used in a calculator mode of operation: and the touch screen means further including means for enabling a user to transfer between the titration screen and the calculator screen during titration procedures.

25. A system as recited in claim 24, wherein the touch screen means includes:

a plurality of calculator screens, each calculator screen corresponding to a respective one of the infusion pump modules; and means for enabling a user to transfer from the titration screen to the calculator screen corresponding to a selected one of the infusion pump modules.

* * * * *